United States Patent
Poundarik (10) Patent No.: US 10,934,342 B1
(45) Date of Patent: Mar. 2, 2021

(54) METHOD FOR MANUFACTURE OF DEMINERALIZED BONE MATERIAL

(71) Applicant: OrthoGraft Pvt. Ltd., Gujarat (IN)

(72) Inventor: Atharva Poundarik, Gujarat (IN)

(73) Assignee: OrthoGraft Pvt. Ltd.

( * ) Notice: Subject to any disclaimer, the term of this patent is extended or adjusted under 35 U.S.C. 154(b) by 0 days.

(21) Appl. No.: 16/192,773

(22) Filed: Nov. 15, 2018

Related U.S. Application Data (60) Provisional application No. 62/587,424, filed on Nov. 16, 2017.

(51) Int. Cl.
  *C07K 14/78* (2006.01)
  *C07K 1/36* (2006.01)

(52) U.S. Cl.
  CPC .............. *C07K 14/78* (2013.01); *C07K 1/36* (2013.01)

(58) Field of Classification Search
  None
  See application file for complete search history.

(56) References Cited

U.S. PATENT DOCUMENTS

| 7,781,158 B2 * | 8/2010 | Yu | C07K 14/78 435/1.1 |
| 2009/0269388 A1 * | 10/2009 | Sunwoo | A61L 27/222 424/423 |
| 2011/0020864 A1 * | 1/2011 | Huang | C07K 14/78 435/68.1 |
| 2012/0134949 A1 * | 5/2012 | Brown | A61L 27/3683 424/70.14 |

* cited by examiner

*Primary Examiner* — Michelle F. Paguio Frising
(74) *Attorney, Agent, or Firm* — Steven A. Wood, Esq.

(57) ABSTRACT

The invention comprises several embodiments of a multi-step method for extracting mineral and protein components from a mineralized biocomposite material, including at least the steps of: extracting proteins and minerals from a material into a first solution by contacting or immersing it with the first solution, comprising one or more of a demineralization solution and a salt solution; obtaining a first solid portion from the first solution, by separating the solid and liquid portions; extracting proteins and minerals from the first solid portion into a second solution by contacting or immersing it with the second solution, comprising one or more of a demineralization solution and a salt solution; and obtaining a second solid portion from the second solution by separating the liquid and solid portions. Each of these embodiments may be operated in succession to any of the other embodiments to create custom optimized extraction processes.

20 Claims, 5 Drawing Sheets

METHOD FOR MANUFACTURE OF DEMINERALIZED BONE MATERIAL

CROSS REFERENCE TO RELATED APPLICATION

This application is a non-provisional of and claims the benefit under 35 U.S.C. § 119(e) of the earlier filing date of U.S. Provisional Application Ser. No. 62/587,424, filed on Nov. 16, 2017, which is hereby incorporated in entirety by reference.

BACKGROUND

1. Field

The present invention relates to a novel multi-step process for protein extraction and demineralization of mineralized biocomposites, including hard tissues such as bone and teeth; calcified soft tissues such as cartilage, tendon, ligament, vertebral disc; and other naturally occurring mineralized biocomposites.

2. Description of Related Art

Naturally occurring mineralized materials incorporate an inorganic or mineral component into a softer organic matrix to form mineralized biocomposites. Typically, these mineralized materials form a protective shield or structural support. Bone, mollusc shells, coral, deep sea sponge, radiolarians, diatoms, antler bone, tendon, cartilage, tooth enamel and dentin are some examples of mineralized tissues (Biomineralization: Principles and Concepts in Bioinorganic Materials Chemistry, Stephen Mann, 2002). Mineralized tissues may also be a pathological phenomenon, e.g., tumor pathology or kidney stone formation. The mineral component makes the material harder and stiffer. Hydroxyapatite, calcium carbonate, calcium phosphates, silica, calcium oxalate and monosodium urate are examples of minerals found in naturally mineralized materials.

The demineralization of such tissues specifically implies the extraction or separation of the inorganic or mineral component from the remaining organic component. The demineralizing process typically involves placing the bone or other mineralized biocomposite into an acidic solution to dissolve the mineral component and then separating the insoluble component (e.g., demineralized bone matrix, in the case where the mineralized biocomposite is bone) from the solvent. Currently, the process of demineralization and protein extraction is typically carried out in a single step.

It remains desirable to have a novel method of processing bone and other mineralized biocomposite materials, with improved protein extraction, for the manufacture of demineralized biocomposites containing lower levels of proteins than possible using current methods and processes.

SUMMARY OF THE INVENTION

The following is a summary of the invention in order to provide a basic understanding of some aspects of the invention. This summary is not intended to identify all key or critical elements of the invention or to delineate the entire scope of the invention. Its sole purpose is to present some concepts of the invention in a simplified form as a prelude to the more detailed description that is presented later.

Reference throughout this specification to "one embodiment" or "an embodiment" means that a particular feature, structure, or characteristic described in connection with an embodiment is included in at least one embodiment of claimed subject matter. Thus, appearances of phrases such as "in one embodiment" or "an embodiment" in various places throughout this specification are not necessarily all referring to the same embodiment. Furthermore, particular features, structures, or characteristics may be combined in one or more embodiments.

The present invention provides a novel multi-step process for manufacture of demineralized biocomposite materials, such as demineralized bone matrix (DBM) and other demineralized biocomposites. The process includes extracting minerals and proteins, is not limited to bone tissue and can be adapted to other biomineralized materials without undue experimentation. Thus, the starting material for demineralization can be, but is not limited to hard tissues such as bone and teeth; calcified soft tissues such as cartilage, tendon, ligament, vertebral disc; and other naturally occurring mineralized biocomposites.

These and other aspects of the present invention are realized in a unique method for demineralizing biocomposites and extracting protein therefrom, as well as a method for manufacture thereof as shown and described in the following figures and related description. Additional features and advantages of the invention will be set forth in the detailed description which follows, taken in conjunction with the accompanying drawings, which together illustrate by way of example, the features of the invention.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention.

It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed so as to enable one skilled in the art to practice the present invention. These, and other, aspects and objects of the present invention will be better appreciated and understood when considered in conjunction with the following description and the accompanying drawings.

It should be understood, however, that the following description, while indicating preferred embodiments of the present invention and numerous specific details thereof, is given by way of illustration and not of limitation. The drawings and following description are exemplary of various aspects of the invention and are not intended to narrow the scope of the appended claims.

Many changes and modifications may be made within the scope of the present invention without departing from the spirit thereof and the invention includes all such modifications. For instance, although the detailed description deals primarily with demineralization of bone materials, the invention is intended to cover demineralization and protein extraction for many different types of mineralized biocomposites, such as biomineralized or calcified tissues, including mollusk shells, crustacean shells, deep sea sponge, coral, radiolarians, diatoms, antler bone, connective tissue, calcified soft tissues such as cartilage, tendon, ligament, vertebral discs and other soft tissues, hard tissues such as bone and teeth, tooth enamel and dentin, pathologically mineralized tissue, and other naturally occurring mineralized biocomposites.

The novelty in this invention is the extraction of proteins from biocomposite matrices using demineralization and salt solutions in a multi-step process. Broadly, demineralization and protein extraction are carried out using acidic and salt solution extraction steps. Advantages of the process include improved ability to remove a greater amount of proteins from the biocomposite matrix.

In one embodiment and in the case of bone, first, pulverized bone will be contacted with a demineralizing solution, e.g., a solution of acidic pH, until desired levels of demineralization are achieved. By the nature of the demineralization step, some proteins will also be removed from the biocomposite material.

Subsequently, the acidic solution containing extracted proteins and minerals will be separated from particles of the demineralized bone matrix (DBM). Second, the DBM particles will be contacted with a salt solution until desired levels of extraction of collagen-bound protein is achieved, following which a second solid-liquid separation is performed.

Demineralization step: Since the solubility of the mineral component of bone (consisting primarily of hydroxyapatite) has a very strong dependence on pH of the demineralization solution (extractant) [Moreno et al. 1968], an operating pH range of 2 to 7 will be utilized. Various demineralization solutions mentioned below will be used for this process. The bone proteins in the extractant may be subsequently purified or concentrated.

Salt extraction step: The salt extraction step in this invention comprises a high ionic strength salt solution to extract various residual proteins that have not yet been extracted from bone and biocomposite matrices during the demineralization step. This step ensures that the proteins that are bound to the organic matrix of bone, largely collagen, are extracted. The salt extraction solution will have a pH range from 5.0 to 8.0 and will primarily consist of a concentrated solution of phosphate or chloride or sulfate salts of sodium or potassium or ammonium or combinations thereof. The bone proteins in the extractant may be subsequently purified or concentrated.

The following variables may be optimized to attain maximum extraction of proteins that may be bound to the collagen matrix and the mineralized components of bone:

Strength of demineralization solution: 0.005 M to 15 M;
pH range of demineralization solutions: 2-7;
Demineralization solution compositions may comprise one or more acids or acid-based solutions (as detailed below); and one or more salt solutions;
Salt solution compositions: may comprise one or more salt solutions (as detailed below);
Strength of salts in a salt solution: 0.005 M to 15 M; (Anions: citrate$^{3-}$, SO$_4^{2-}$, tartrate$^{2-}$, HPO$_4^{2-}$, CrO$_4^{2-}$, acetate$^-$, HCO$^{3-}$, Cl$^-$, NO$^{3-}$, ClO$^{3-}$; Cations: Mg$^+$, Na$^+$, K$^+$, NH$^{4+}$),
Extraction temperatures 0° C. to 50° C.
Extraction time 10 min to 14 days
Bone particle sizes 1 μm to 10000 μm
Agitation or stirring of solution (10-10000 RPM)

Suitable acids for demineralization solutions include, but are not limited to: organic acids such as formic acid, acetic acid, citric acid, or propionic acid; inorganic acids such as hydrochloric acid, phosphoric acid or sulphuric acid; tissue-compatible hydroxyl-carboxylic acids such as citric acid, gluconic acid, tartaric acid, fumaric acid and malic acid; acidic substances that chelate calcium such as ethylenediaminetetraacetic acid (EDTA), nitriloacetic acid, succinic acid, and heparin.

Furthermore, acid demineralizing solutions may also include solutions of one or more acids in one or more alcohols. Any alcohol such as, for example, ethanol and isopropyl alcohol may be used. Other suitable acid solutions may include solutions of one or more acids in glycerol or other organic and/or metal chelator.

Moreover, demineralization solutions have been shown to extract minerals and proteins from biocomposite materials, like bone, as described in patent serial no. U.S. Pat. No. 8,753,689 B2, Method of making demineralized bone particles, to Morris, et al., and by Pietrzak and Ali, in *The Extraction and Measurement of Bone Morphogenetic Protein 7 From Bovine Cortical Bone as a Function of Particle Size*. Journal of Craniofacial Surgery, 26(1), 296-299, (2015).

Salt solutions as used in this invention may comprise, either individually or in combination, but are not limited to the anionic and cationic components of the Hofmeister series (Anions: citrate$^{3-}$, SO$_4^{2-}$, tartrate$^-$, HPO$_4^{2-}$, CrO$_4^{2-}$, acetate$^-$, HCO$^{3-}$, Cl$^-$, NO$^{3-}$, ClO$^{3-}$; Cations: Mg$^{2+}$, Li$^+$, Na$^+$, K$^+$, NH$^4$). For example, the salt solution can comprise one or more of phosphate, chloride or sulfate salts of sodium or potassium or ammonium, or combinations thereof.

Moreover, salt solutions have been shown to extract proteins from biological materials, as described by Rivero, et al., in "*Simple salting-out method for DNA extraction from formalin-fixed, paraffin-embedded tissues*, Pathology-Research and Practice, 202(7), 523-529 (2006).

Exemplary demineralization solutions, as disclosed in this application, were tested for demineralization and protein extraction from mineralized bone tissue over a span of four to twenty-four (4-24) hours. These tests demonstrated that protein extraction can vary greatly with the type of solution employed. For example, up to 15-20% of bone protein was extracted into solution using a first exemplary demineralization solution, and only up to 4-5% of bone protein was extracted into solution using a second exemplary demineralization solution. This demonstrates a substantial difference in the capacity of different solutions to extract protein (4:1 ratio in this case). Thus, protein extraction can be optimized by selecting an appropriate arrangement demineralization steps and/or salt treatment steps.

As one embodiment of the invention, the following steps will be employed in the method:

1. Contact between the bone and demineralization solution, or subsequently, between the resultant DBM and salt solution, will be established for a specific period of time in a stirred tank with the agitator at a RPM of 10-10000 for a specific period of time at a specific temperature. As an alternate to the stirred tank, solid liquid contact in Step 1 may involve the use of a packed column of bone powder or DBM granules, for demineralization and salt solution extraction steps.
2. The extractant (i.e., the solution used to extract organic tissue components) will be separated from the solids following extraction using centrifugation or decantation or depth filtration or a combination of these methods.

The capability of the present invention to extract a greater amount of proteins from the starting biocomposite tissue materials, such as bone, consequently results in lower protein content of the DBM. The protein content of DBM made by the multi-step method of the present invention, following extraction of proteins by one or more iterations of demineralization and salt solutions is significantly lower than any other commercially available DBM products.

Figure 1:
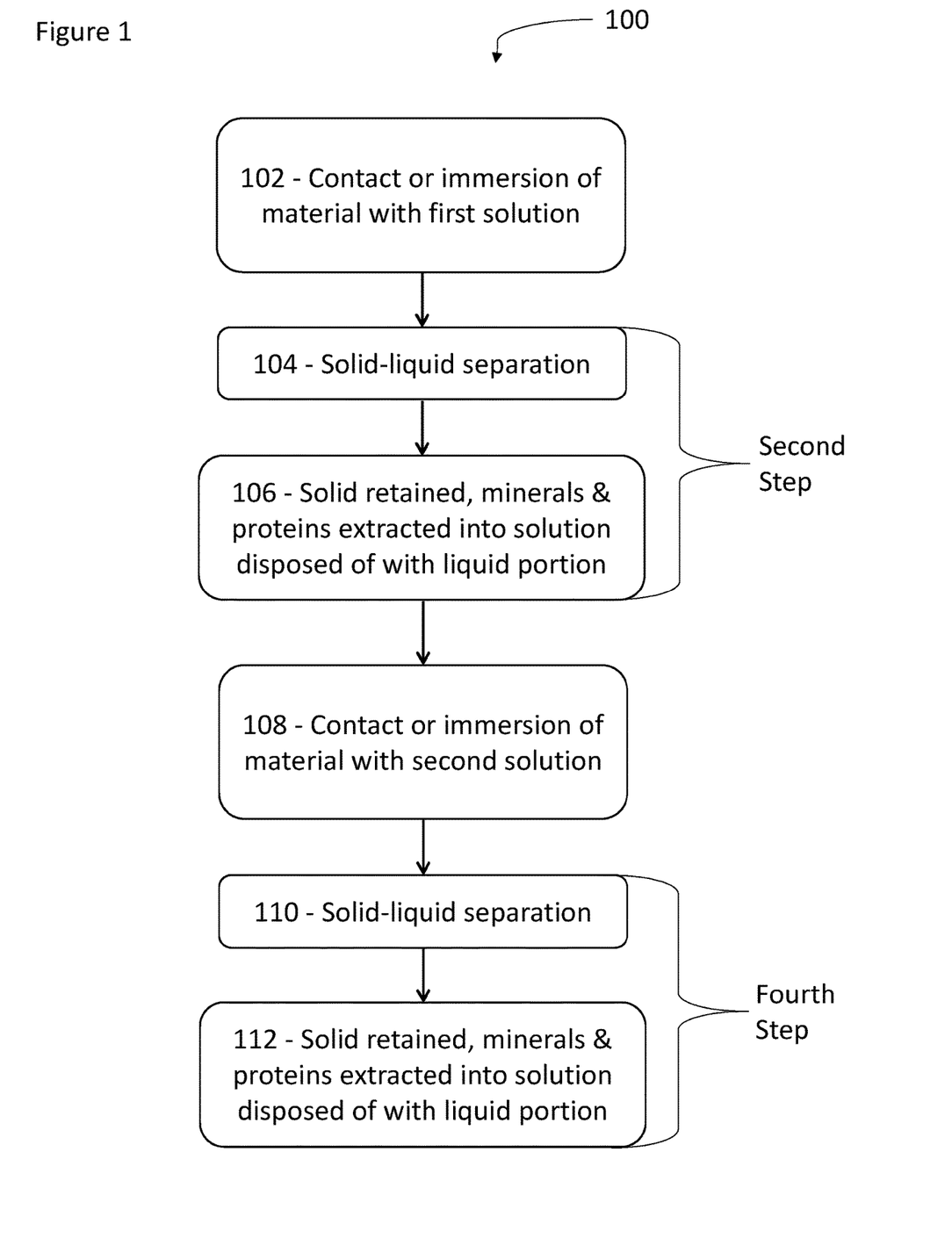
FIG. 1. In a first embodiment, any series of steps can be performed, utilizing either demineralization or salt extraction steps, in any order. The minerals and proteins may then be extracted from both solutions. This process can be repeated as necessary for optimized extraction of mineral and protein components.

A first preferred embodiment of the present invention is shown in FIG. 1. This first preferred embodiment comprises a multi-step method 100 of extracting mineral content, protein content and a solid component from a mineralized biocomposite material, including at least the steps of: 1) extracting one or more of proteins and minerals from a material into a first solution by one or more of contacting and immersing the material with the first solution 102 one or more times, wherein the first solution comprises one or more of a demineralization solution and a salt solution; 2) obtaining a first solid portion of material from the first solution 106, by separating the solid and liquid portions 104; 3) extracting one or more of proteins and minerals from the first solid portion of material into a second solution by one or more of contacting and immersing the first solid portion of material with the second solution 108 one or more times, wherein the second solution comprises one or more of a demineralization solution and a salt solution; and 4) obtaining a second solid portion of material from the second solution 112 by separating the liquid and solid portions 110.

In this first preferred embodiment, the mineralized biocomposite material may be a crushed or pulverized material, such as biomineralized or calcified tissues, comprising one or more of mollusk shells, crustacean shells, deep sea sponge, coral, radiolarians, diatoms, antler bone, connective tissue, calcified soft tissues such as cartilage, tendon, ligament, vertebral discs and other soft tissues, hard tissues such as bone and teeth, tooth enamel and dentin, pathologically mineralized tissue, and other naturally occurring mineralized biocomposites.

In this first preferred embodiment, the first or second solution may comprise a demineralization solution including, without limitation, one or more of the following acids: hydrochloric acid phosphoric acid, sulfuric acid and other inorganic acids; acetic acid, formic acid, citric acid, propionic acid and other organic acids; gluconic acid, tartaric acid, fumaric acid, malic acid and other hydroxy carboxylic acids; ethylenediaminetetraacetic acid (EDTA), nitriloacetic acid, succinic acid, heparin and other metal and calcium chelating acids; as well as acid alcohol solutions, such as ethanol and isopropanol; and glycerol.

Further, the strength of the acids included in the demineralization solutions may be between 0.005 M to 15 M. In addition, the demineralization solution has a pH in the range of 2 to 7. The demineralization solution may additionally comprise a salt solution including, without limitation, one or more of the following salts: phosphate, chloride and sulfate salts of one or more of sodium, potassium, and ammonium.

The demineralization solution may additionally comprise a salt solution comprising one or more of the following anionic components including, without limitation, citrate$^{3-}$, $SO_4^{2-}$, tartrate$^{2-}$, $HPO_4^{2-}$, $CrO_4^{2-}$, acetate$^-$, $HCO^{3-}$, $Cl^-$, $NO^{3-}$, $ClO^{3-}$, and one or more of the following cationic components including, without limitation, $Mg^+$, $Li^+$, $Na^+$, $K^+$, $NH^{4+}$.

Furthermore, the first or second solutions may comprise a salt solution including, without limitation, one or more of the following salts: phosphate, chloride and sulfate salts of one or more of sodium, potassium, and ammonium. In addition, the first or second solutions may comprise a salt solution comprising one or more of the following anionic components including, without limitation, citrate$^{3-}$, $SO_4^{2-}$, tartrate$^-$, $HPO_4^{2-}$, $CrO_4^{2-}$, acetate$^-$, $HCO^{3-}$, $Cl^-$, $NO^{3-}$, $ClO^{3-}$, and one or more of the following cationic components including, without limitation, $Mg^+$, $Li^+$, $Na^+$, $K^+$, $NH^{4+}$.

In this first preferred embodiment, the strength of the one or more salts included in the salt solutions may be between 0.005 M and 15 M.

In addition, the extraction temperature may be between 0° C. to 50° C. Further, the extraction time may be between 10 min to 14 days.

Furthermore, the liquid to solid ratio for the proportion of the volume of the first or second solutions containing a solid portion of the material may vary from 2 ml/gm to 20000 ml/gm.

The original particle size of the mineralized biocomposite material may range from 1 μm to 10000 μm.

This preferred embodiment may further include the step of performing agitation or stirring of the solution within a range of 10-10000 revolutions per minute, to accelerate demineralization and protein extraction.

This first preferred embodiment may further include the steps of separating the solid portion of material from the first and second solution using one or more of centrifugation, filtration and decantation. The method of this preferred embodiment may further include repeating the first, second, third and fourth steps one or more successive times. Moreover, the first and second solutions in successive repetitions of the first and third steps may, respectively, comprise one or more of the same or different demineralization and salt solutions.

Figure 2:
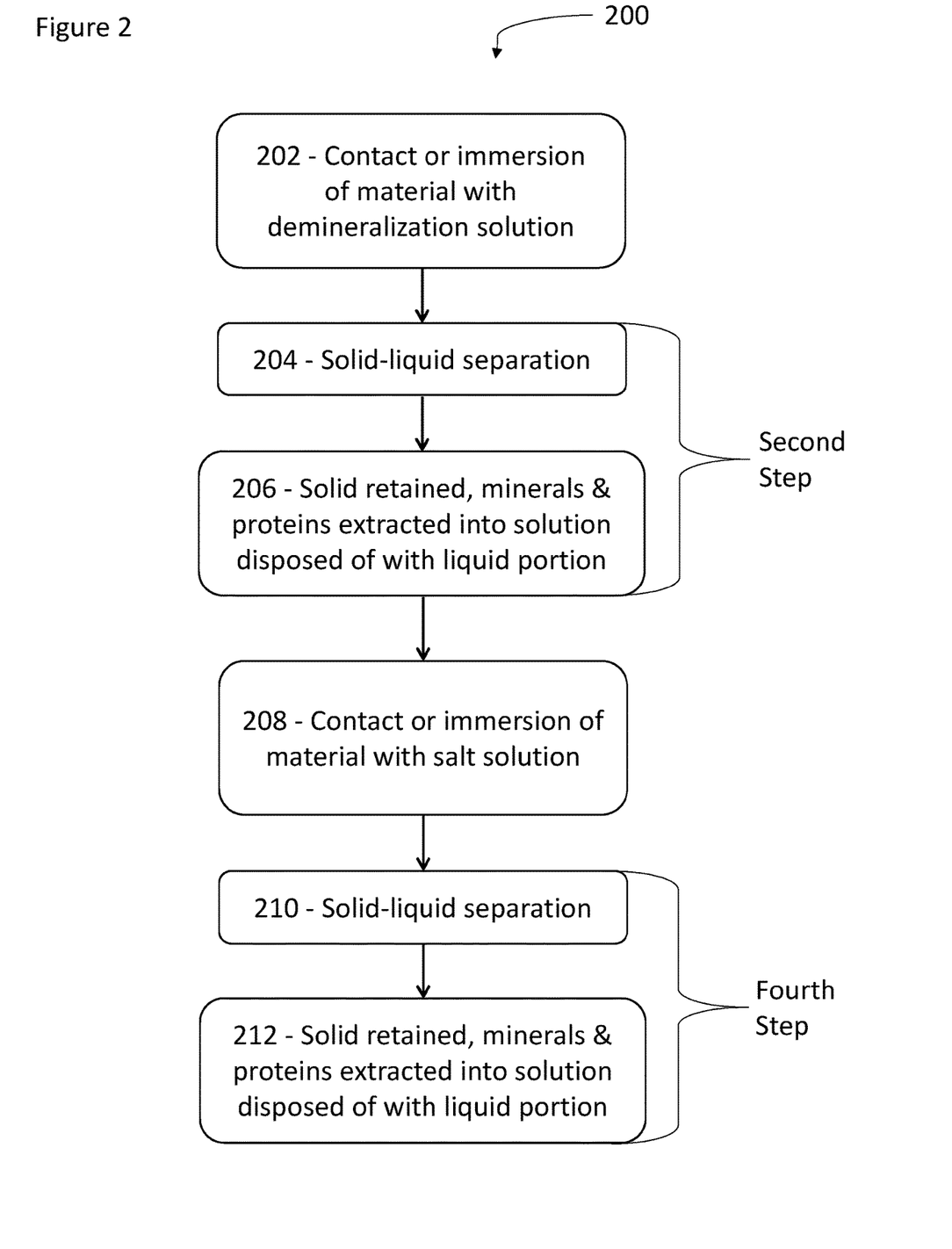
FIG. 2. In a second embodiment, both demineralization and salt extraction steps can be performed with the demineralization step coming prior to the salt extraction step. The minerals and proteins may then be extracted from both solutions. This process can be repeated as necessary for optimized extraction of mineral and protein components.

A second preferred embodiment of the present invention is shown in FIG. 2. This second preferred method comprises a multi-step method 200 of extracting mineral content, protein content and a solid component from a mineralized biocomposite material, including at least the steps of: 1)

extracting proteins and minerals from a material into a first solution, comprising a demineralization solution, by one or more of contacting and immersing the material with the first solution 202 one or more times; 2) obtaining a first solid portion of material from the first solution 206, by separating the solid and liquid portions 204; 3) extracting proteins and minerals from the first solid portion of material into a second solution, comprising a salt solution, by one or more of contacting and immersing the first solid portion of material with the second solution 208 one or more times; 4) obtaining a second solid portion of material from the second solution 212 by separating the liquid and solid portions 210.

The method of this other preferred embodiment may further include repeating the first, second, third and fourth steps one or more successive times. Moreover, the first and second solutions in successive repetitions of the first and third steps may, respectively, comprise one or more of the same or different demineralization and salt solutions.

Figure 3:
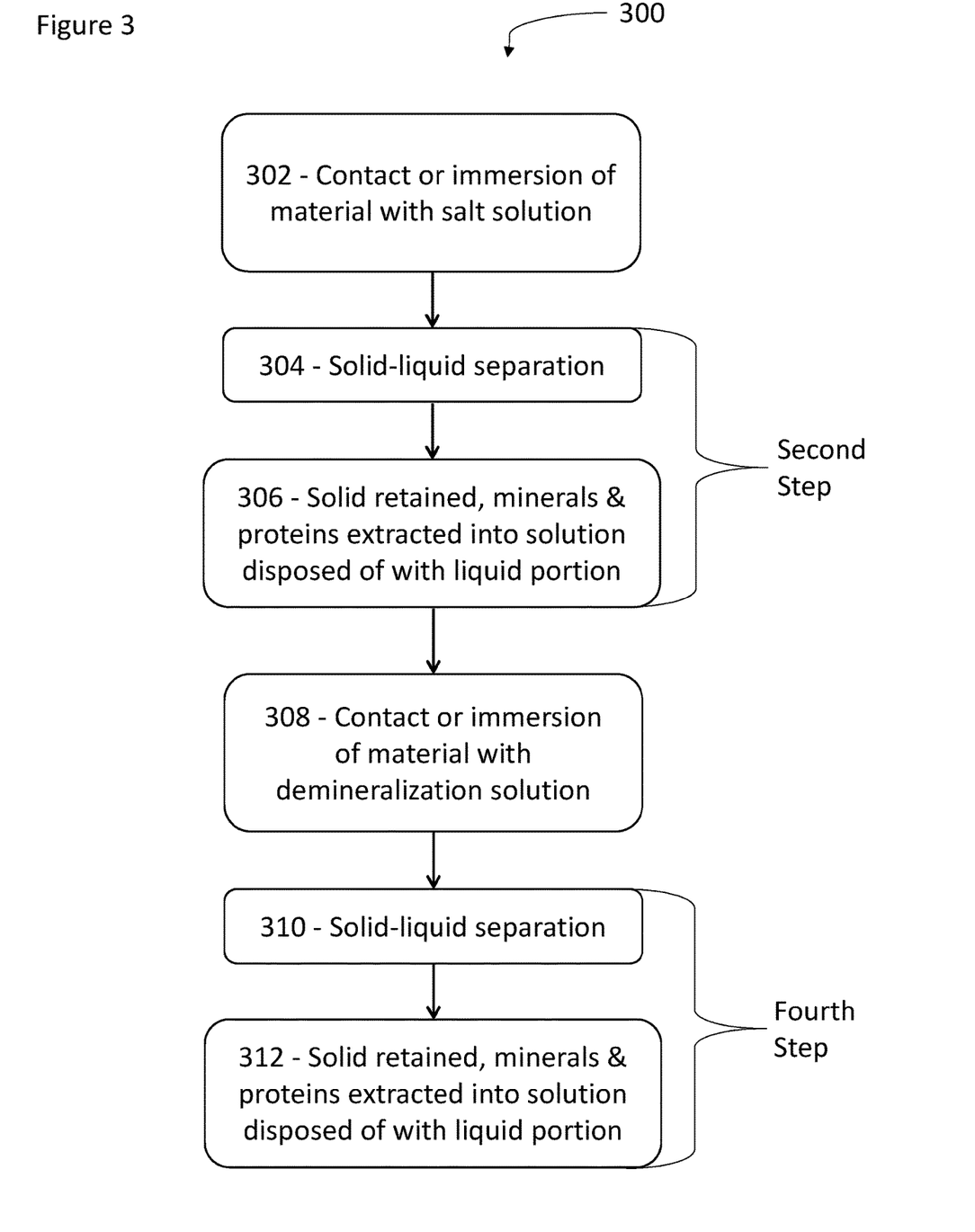
FIG. 3. In a third embodiment, both salt extraction and demineralization steps can be performed with the salt extraction step coming prior to the demineralization step. The minerals and proteins may then be extracted from both solutions. This process can be repeated as necessary for optimized extraction of mineral and protein components.

A third preferred embodiment of the present invention is shown in FIG. 3. This third preferred embodiment comprises a multi-step method 300 of extracting mineral content, protein content and a solid component from a mineralized biocomposite material, including at least the steps of: 1) extracting proteins and minerals from a material into a first solution, comprising a salt solution, by one or more of contacting and immersing the material with the first solution 302 one or more times; 2) obtaining a first solid portion of material from the first solution 306, by separating the solid and liquid portions 304; 3) extracting proteins and minerals from the first solid portion of material into a second solution, comprising a demineralization solution, by one or more of contacting and immersing the first solid portion of material with the second solution 308 one or more times; and 4) obtaining a second solid portion of material from the second solution 312 by separating the liquid and solid portions 310.

The method of this third preferred embodiment may further include repeating the first, second, third and fourth steps one or more successive times. Moreover, the first and second solutions in successive repetitions of the first and third steps may, respectively, comprise one or more of the same or different demineralization and salt solutions.

Figure 4:
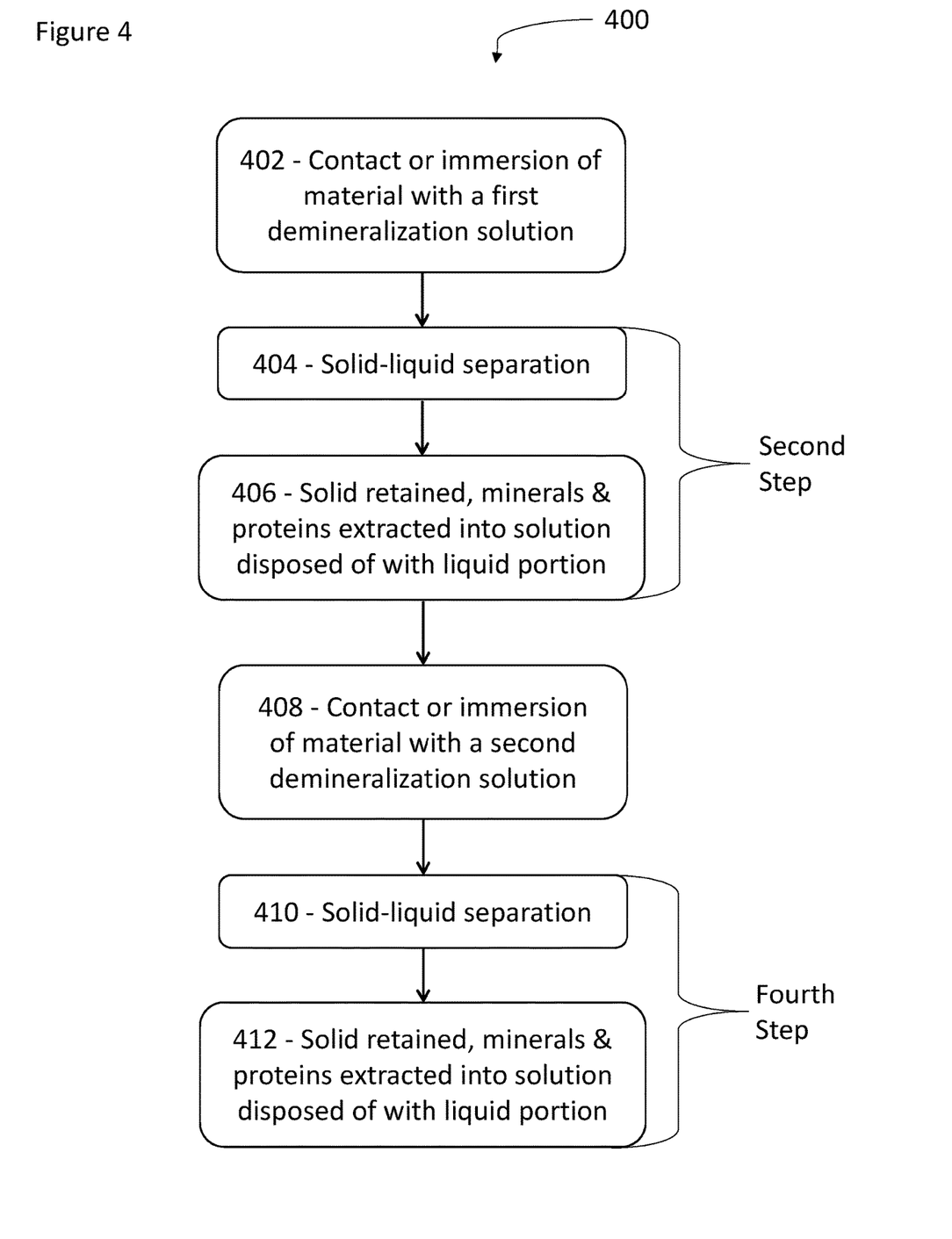
FIG. 4. In a fourth embodiment, only demineralization steps are performed with the same or different demineralization solutions. The minerals and proteins may then be extracted from both solutions. This process can be repeated as necessary for optimized extraction of mineral and protein components.

A fourth preferred embodiment of the present invention is shown in FIG. 4. This fourth preferred embodiment comprises a multi-step method 400 of extracting mineral content, protein content and a solid component from a mineralized biocomposite material, including at least the steps of: 1) extracting proteins and minerals from a material into a first solution, comprising a demineralization solution, by one or more of contacting and immersing the material with the first solution 402 one or more times; 2) obtaining a first solid portion of material from the first solution 406, by separating the solid and liquid portions 404; 3) extracting proteins and minerals from the first solid portion of material into a second solution, comprising a demineralization solution, by one or more of contacting and immersing the first solid portion of material with the second solution 408 one or more times; and 4) obtaining a second solid portion of material from the second solution 412 by separating the liquid and solid portions 410.

The method of this fourth preferred embodiment may further include repeating the first, second, third and fourth steps one or more successive times. Moreover, the first and second solutions in successive repetitions of the first and third steps may, respectively, comprise one or more of the same or different demineralization solutions.

Figure 5:
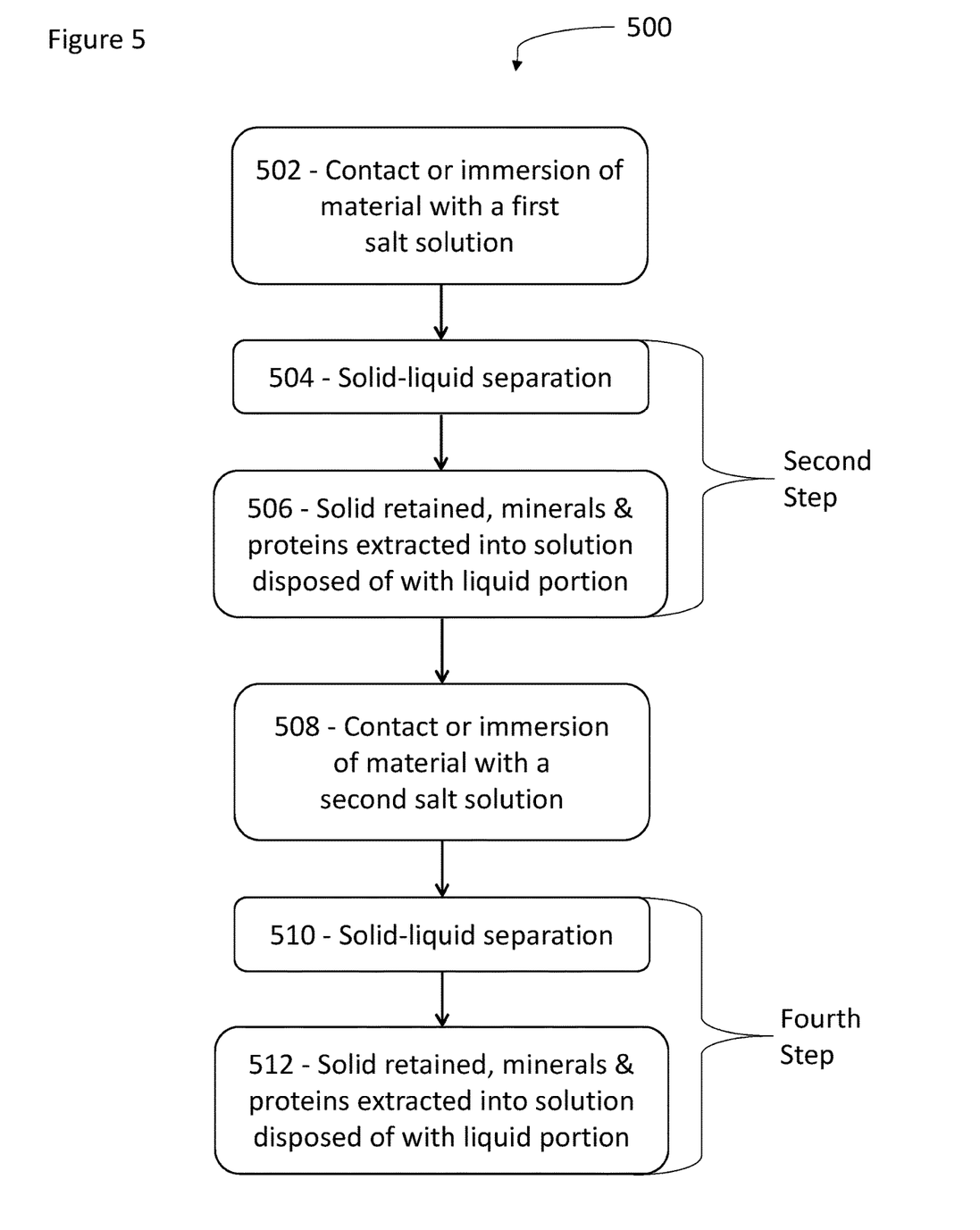
FIG. 5. In a fifth embodiment, only salt extraction steps are performed with the same or different salt solutions. The minerals and proteins may then be extracted from both solutions. This process can be repeated as necessary for optimized extraction of mineral and protein components.

A fifth preferred embodiment of the present invention is shown in FIG. 5. This fifth preferred embodiment comprises a multi-step method 500 of extracting mineral content, protein content and a solid component from a mineralized biocomposite material, including at least the steps of: 1) extracting proteins and minerals from a material into a first solution, comprising a salt solution, by one or more of contacting and immersing the material with the first solution 502 one or more times; 2) obtaining a first solid portion of material from the first solution 506, by separating the solid and liquid portions 504; 3) extracting proteins and minerals from the first solid portion of material into a second solution, comprising a salt solution, by one or more of contacting and immersing the first solid portion of material with the second solution 508 one or more times; and 4) obtaining a second solid portion of material from the second solution 512 by separating the liquid and solid portions 510.

The method of this fifth preferred embodiment may further include repeating the first, second, third and fourth steps one or more successive times. Moreover, the first and second solutions in successive repetitions of the first and third steps may, respectively, comprise one or more of the same or different salt solutions.

Moreover, each of these embodiments may be operated in any successive order with respect to any of the other embodiments to create customized, optimized extraction processes. Further, these customized processes can be repeated as necessary for optimized extraction of mineral and protein components.

It should be understood that, although specific embodiments have just been described, the claimed subject matter is not intended to be limited in scope to any particular embodiment or implementation. In the preceding description, various aspects of claimed subject matter may have been described. For purposes of explanation, specific numbers, systems, or configurations may have been set forth to provide a thorough understanding of claimed subject matter.

However, it should be apparent to one skilled in the art having the benefit of this disclosure that claimed subject matter may be practiced without those specific details. In other instances, features that would be understood by one of ordinary skill in the art were omitted or simplified so as not to obscure claimed subject matter.

While certain features have been illustrated or described herein, many modifications, substitutions, or equivalents may not occur to those skilled in the art. It is, therefore, to be understood that the appended claims are intended to cover all such modifications or changes as fall within the true spirit of the claimed subject matter.

What is claimed is:

1. A multi-step method of extracting mineral content, protein content and a solid component from a mineralized biocomposite material, comprising the steps of:
   a first step of extracting one or more of proteins and minerals from a material into a first solution by one or more of contacting and immersing the material with the first solution one or more times, wherein the first solution comprises a demineralization solution including one or more of the following acid constituents: hydrochloric acid, ethylenediaminetetraacetic acid, formic acid, acetic acid, citric acid and propionic acid combined with one or more salts including sodium, magnesium and potassium salts of acetate, citrate and phosphate;
   a second step of obtaining a first solid portion of material from the first solution;
   a third step of extracting one or more of proteins and minerals from the first solid portion of material into a second solution by one or more of contacting and immersing the first solid portion of material with the second solution one or more times, wherein the second solution comprises a demineralization solution including one or more of the following acid constituents: hydrochloric acid, ethylenediaminetetraacetic acid, formic acid, acetic acid, citric acid and propionic acid, combined with one or more salts including sodium, magnesium and potassium salts of acetate, citrate and phosphate;

a fourth step obtaining a second solid portion of material from the second solution.

2. The method of claim 1, wherein the mineralized biocomposite material is a crushed or pulverized material comprising one or more of mollusk shells, crustacean shells, deep sea sponge, coral, radiolarians, diatoms, antler bone, connective tissue, calcified soft tissues including cartilage, tendon, ligament, vertebral discs and other soft tissues, hard tissues such as bone and teeth, tooth enamel and dentin, pathologically mineralized tissue, and other naturally occurring mineralized biocomposites.

3. The method of claim 1, wherein the demineralization solution used in the first step comprises acid constituents limited to one or more of hydrochloric acid, acetic acid, and citric acid.

4. The method of claim 3, wherein a strength of the one or more acids included in the demineralization solutions is between 0.005 M to 15 M.

5. The method of claim 3, wherein the demineralization solution has a pH in the range of 2 to 7.

6. The method of claim 3, wherein the demineralization solution used in the third step comprises one or more salts limited to sodium, magnesium and potassium salts of phosphate, acetate and citrate.

7. The method of claim 3, wherein the first or second demineralization solution comprises a salt solution including one or more of the following anionic components limited to citrate$^{3-}$, $HPO_4^{2-}$, $HPO_4^-$, $H_2PO_4^-$, $PO_3^-$, acetate$^-$, and one or more of the following cationic components limited to $Mg^{2+}$, $Na^+$, $K^+$.

8. The method of claim 1, wherein the second solution comprises one or more salts limited to sodium, magnesium and potassium salts of acetate, phosphate and citrate.

9. The method of claim 1, wherein the second solution comprises a salt solution including one or more of the following anionic components limited to citrate$^{3-}$, $HPO_4^{2-}$, $HPO_4^-$, $H_2PO_4^-$, $PO_3^-$, acetate$^-$, and one or more of the following cationic components including $Mg^{2+}$, $Na^+$, $K^+$.

10. The method of claim 1, wherein a strength of the one or more salts included in the salt solutions is between 0.005 M and 15 M.

11. The method of claim 1, wherein an extraction temperature of between 0° C. to 50° C. is used for all extraction steps.

12. The method of claim 1, wherein an extraction time of between 10 min to 14 days is used for all extraction steps.

13. The method of claim 1, wherein a liquid to solid ratio for the proportion of the volume of the first or second solution containing a solid portion of the material varies from 2 ml/gm to 20000 ml/gm.

14. The method of claim 1, wherein an original particle size of the mineralized biocomposite material varies from 1 μm to 10000 μm.

15. The method of claim 1, further including the step of performing agitation or stirring all of the solutions used in all extraction steps within a range of 10-10000 revolutions per minute, thereby accelerating demineralization and protein extraction.

16. The method of claim 1, further including the steps of separating the respective first or second solid portion of material from the first and second solutions using one or more of centrifugation, filtration and decantation.

17. The method of claim 1, wherein the method further includes repeating the first, second, third and fourth steps one or more successive times.

18. The method of claim 17, wherein the first and second solutions in successive repetitions of the first and third steps, respectively, comprise one or more of the same or different demineralization solutions.

19. The method of claim 18, wherein the first solution comprises a demineralization solution, and wherein the second solution comprises solely a salt solution.

20. The method of claim 1, wherein the method further comprises successive multiple extractions using one or more of the same and different acid-based demineralization solutions, followed by a final treatment using a solely salt solution before obtaining a final solid portion.

* * * * *